US009333332B2

(12) United States Patent
Eisenkolb et al.

(10) Patent No.: US 9,333,332 B2
(45) Date of Patent: May 10, 2016

(54) VALVE FOR MEDICAL INSTRUMENT

(75) Inventors: Peter Eisenkolb, Wohnsitz (DE); Andreas Efinger, Wohnsitz (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 837 days.

(21) Appl. No.: 11/230,149

(22) Filed: Sep. 19, 2005

(65) Prior Publication Data

US 2006/0069352 A1 Mar. 30, 2006

(30) Foreign Application Priority Data

Sep. 17, 2004 (DE) ........................ 10 2004 045 586

(51) Int. Cl.
*A61M 39/06* (2006.01)
*A61M 39/22* (2006.01)
*A61B 17/34* (2006.01)

(52) U.S. Cl.
CPC ........ *A61M 39/0606* (2013.01); *A61B 17/3462* (2013.01); *A61B 17/3498* (2013.01); *A61M 39/228* (2013.01); *A61M 2039/066* (2013.01); *A61M 2039/0626* (2013.01); *A61M 2039/0633* (2013.01); *A61M 2039/0686* (2013.01)

(58) Field of Classification Search
CPC ............... A61M 2039/0633; A61M 2039/062; A61M 2039/066; A61M 2039/0673; A61M 2039/2426; A61M 39/0606; A61M 39/228; A61M 2039/0626; A61M 2039/0686; A61B 17/3462; A61B 17/3498
USPC .............. 604/30, 31, 33, 34, 99, 164.01, 237, 604/246, 247, 250, 278, 288, 323, 335, 533, 604/99.04, 158, 167, 1–167.04, 167.06, 604/236, 256, 288.03; 251/5, 61, 149.1, 251/149.3, 294, 342, 903, 12, 335.1, 343, 251/344, 901; 137/247–254, 844, 853, 505, 137/508, 511, 843, 847, 851, 852
See application file for complete search history.

(56) References Cited

U.S. PATENT DOCUMENTS

| | | | | | |
|---|---|---|---|---|---|
| 4,473,067 | A | * | 9/1984 | Schiff | 600/18 |
| 5,092,857 | A | * | 3/1992 | Fleischhacker | 604/256 |
| 5,161,773 | A | * | 11/1992 | Tower | 251/5 |
| 5,205,325 | A | * | 4/1993 | Piper | 137/844 |
| 5,251,873 | A | * | 10/1993 | Atkinson et al. | 251/149.1 |
| 5,350,364 | A | * | 9/1994 | Stephens et al. | 604/167.06 |

(Continued)

FOREIGN PATENT DOCUMENTS

| | | |
|---|---|---|
| DE | 693 13 504 | 2/1998 |
| DE | 101 48 572 | 1/2003 |
| WO | 91/12838 | 9/1991 |

*Primary Examiner* — Emily Schmidt
*Assistant Examiner* — Lauren M Peng
(74) *Attorney, Agent, or Firm* — Whitmyer IP Group LLC

(57) ABSTRACT

A valve for medical instruments having a canal configured in a medical instrument and serving as input for at least one additional medical instrument is insulated from a distal-end fluid, whereby the valve housing wherein at least one fluid opening is configured, and positioned in the housing at least one insulating body can be inserted at least partly into the canal. The invention has at least one fluid opening configured in the valve housing by which the fluid can be conducted to the outside of the insulating body such that the fluid opening is so configured that the distal-side fluid can be guided out of the canal to the outside of the insulating body in such a way that the distal-side fluid reshapes the insulating body inward, insulating it, to be essentially perpendicular to the longitudinal direction of the insulating body.

31 Claims, 2 Drawing Sheets

(56) References Cited

U.S. PATENT DOCUMENTS 5,405,336 A * 4/1995 Austin et al. .................. 604/534
5,584,805 A * 12/1996 Sutton ............................. 604/60
5,662,615 A * 9/1997 Blake, III ........... A61B 17/3462 604/167.06
6,887,220 B2 * 5/2005 Hogendijk .................... 604/119
7,241,276 B2 * 7/2007 Argentine et al. ....... 604/167.06
2002/0128604 A1 * 9/2002 Nakajima ................ 604/164.01
2003/0009079 A1 1/2003 Beaufore et al. ................ 600/29
2003/0085373 A1 5/2003 Dehdashtian .............. 251/149.3
2004/0177882 A1 * 9/2004 Vasilev ......................... 137/528
2005/0209572 A1 * 9/2005 Rome et al. ................... 604/250

* cited by examiner 17
3
12
5
12
12
2
1

7
4
3
14
4a
6
19
16
12
5
2
15
18
17
13
7
5
1

VALVE FOR MEDICAL INSTRUMENT

This application claims priority of German Patent Application No. 10 2004 045 586.4 filed on Sep. 17, 2004.

FIELD OF THE INVENTION

The invention relates to a valve for a medical instrument, in particular an endoscopic instrument, for insulating against a distal-side fluid comprising: a canal configured in the medical instrument and serving for the intake of at least one additional medical instrument. The valve has a valve housing that can be inserted at least partially into the canal, so that in the valve housing at least one fluid opening is configured, and the valve has at least one insulating body situated in the valve housing and consisting of an elastic material.

Valves of this type serve to insulate the canal serving for the intake of at least one additional medical instrument in an endoscopic instrument, in particular when no instrument has been inserted into the canal. The canal is insulated in this case against a fluid arising on the distal side, such as in laparoscopy, for instance, a gas serving to shape the pneumo-peritoneum or else, if used with a uretero-renoscope, a liquid.

For the configuration of valves of this type it is a familiar practice, for instance, to configure the insulating body positioned in the valve housing as a so-called Duckbill insulation, in which two insulating lips directed toward the distal end of the valve housing are in contact with one another. These valves configured with insulating bodies of this kind have the disadvantage in practice, among others, that an instrument can be guided through the insulating lips only from one side, namely the proximal side.

A valve of this generic type for medical instruments is known, for instance, from DE 101 48 572. To increase the insulating power of the insulating body consisting of elastic material, it is possible with this known construction to impact the insulating bodies that are in contact with one another by way of the fluid opening from outside with a pressure medium, in particular air. The insulating bodies of this known valve construction ensure good insulation, but the imposition of an external pressure medium involves intense technological and space-intensive effort, which can rarely be achieved, especially in the use of endoscopic instruments.

Patent DE 693 13 504 T2 describes an additional valve arrangement in which the insulating body to be secured in the housing is configured in such a way that the insulating body can be pretensioned by a device, such as a clamping clip, working on the insulating body from outside, in such a way that the insulating body insulates the canal serving for the input of the medical instrument that is to be inserted, when the instrument is not inserted. In addition to the complex structure of this known valve arrangement with steering elements configured on the inside of the insulating body, the use of the pre-tensioning device working from outside on the insulating body is disadvantageous because, for one thing, this device further complicates the structure of this valve and, for another thing, the insulating effect of the valve is exclusively dependent on the tension effect of this device which in its use is subject to wear. Consequently, the object of the invention is to create a valve for medical instruments of the aforementioned type, which is simple in construction and guarantees a reliable automatic insulating effect.

This task is fulfilled by the invention in that the fluid opening is configured so that the distal-side fluid can be guided to the outside of the insulating body in such a way that the distal-side fluid reshapes the insulating body toward the inside while insulating, essentially perpendicular to the longitudinal direction of the insulating body.

As a result of the inventive arrangement, it is possible for the first time to create a self-closing valve that works in the manner of a return valve. The fluid which is to be prevented from exiting by the action of the inventive valve ensures, in turn, by the pressure acting on the insulating body from outside, that the valve is at least closed when no medical instrument is positioned in the canal.

According to a practical embodiment of the invention, it is proposed that the at least one fluid opening is configured as a slit running in the axial direction of the valve housing. To ensure quick and even fluid distribution and thus pressure distribution as well, in the valve housing there are advantageously several, preferably three, slits as fluid openings evenly distributed around the circumference of the valve housing and extending as far as the distal-send end of the valve housing.

So that the insulating effect of the insulating body cannot be weakened or indeed cancelled by the fluid pressure bearing on the insulating body on the distal side, it is proposed with a preferred embodiment of the invention that the surface of the outside of the insulating body standing in contact with the fluid is greater than the distal-side inner surface of the insulating body that is impacted by the fluid.

To configure the insulating body, it is proposed according to a practical embodiment of the invention that on the inside of the insulating body that is to be secured in the valve housing, two insulating lips are configured, arranged opposite to one another, which in the closed position are in contact with one another at least in linear arrangement insulating the canal.

The insulating lips that perform the actual insulation of the insulating body are advantageously of one-piece construction and formed with the material of the insulating body and consist of the same material as the insulating body.

According to a form of the insulating lips that is especially easy to manufacture, they are configured essentially pointing to the middle of the valve housing and convex in cross-section, and on both sides have run-up slopes in order to permit enclosing of a medical instrument from both sides of the insulating body. In addition to this convex-symmetrical arrangement of the insulating lips, other configures, even non-symmetrical ones, are of course possible.

To secure the insulating body in the valve housing, it is proposed with the invention that the insulating body can be secured by at least one configured flange so that it is immovable in the valve housing, and this at least one flange, preferably positioned on the end side for instance, can be inserted into a groove in the housing interior or else forms an end protrusion that secures the position.

In particular, to ensure the insulating effect of the valve with a medical instrument inserted in the canal, it is further proposed with the invention that on the proximal side before the insulating body at least one additional insulating element can be secured in the valve housing. Of course it is also possible to connect the additional insulating element as a one-piece construction with the insulating body or for instance by cementing, to connect it securely with the insulating body.

According to a practical embodiment for configuring this additional insulating element, the element is configured as a disc insulation provided with an opening situated basically centrally, so that the diameter of the opening configured in the disc insulation is smaller than the outer diameter of a medical instrument that is to be inserted through this opening in order to guarantee a fluid-insulating positioning of the insulating disc on the instrument shaft.

To ensure a fluid-insulating and securely positioned insertion of the valve housing into the canal of the endoscopic instrument, it is further proposed with the invention that on the outside of the valve housing at least one insulating element is configured. This insulating element arranged on the outside of the valve housing is advantageously configured as an insulating ring that can be secured in a circular groove configured in the valve housing, in particular as an O-ring made of silicon.

It is finally proposed with the invention that on the valve housing, at least on its proximal side, there should be run-up slopes, which facilitate the introduction of a medical instrument into the canal or the valve.

Additional characteristics and advantages of the invention can be seen from the related illustration, in which an embodiment of an inventive valve for medical instruments is depicted merely schematically.

DETAILED DESCRIPTION OF PREFERRED EMBODIMENTS

Figure 1:
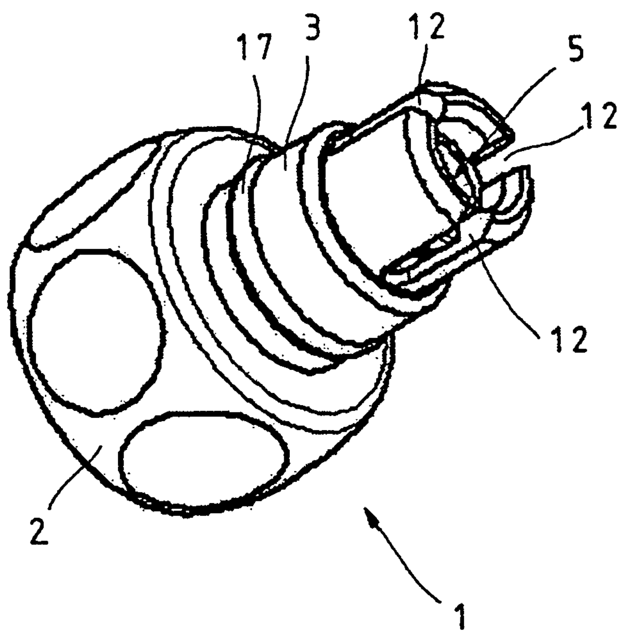
FIG. 1 shows a perspectival view of an inventive valve.
Figure 2:
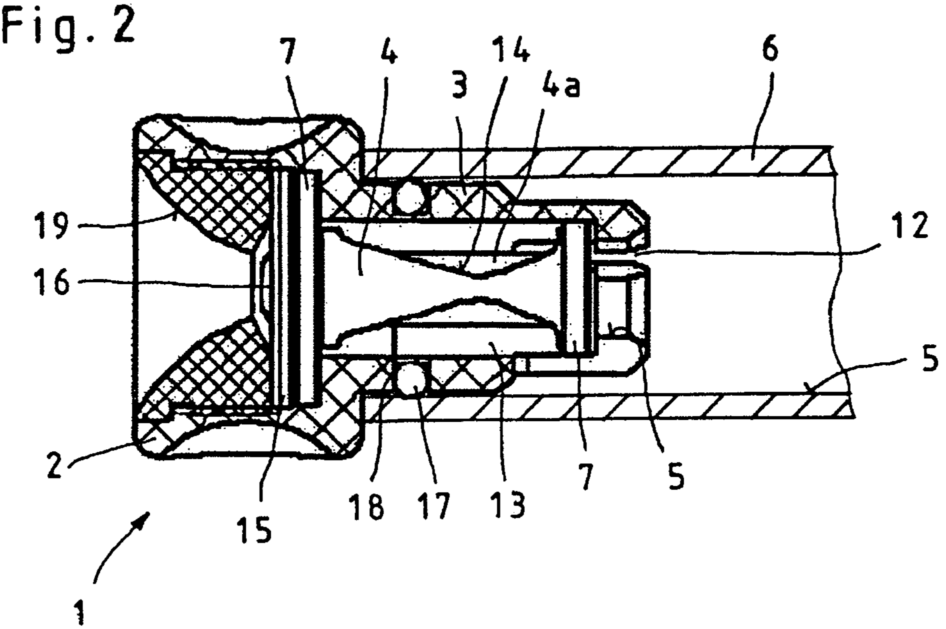
FIG. 2 shows a longitudinal section through the valve shown in FIG. 1.

The illustrations in FIGS. 1 and 2 show a valve which consists essentially of a valve housing 1 with a proximal-side housing head 2 and a housing shaft 3 adjoining it, as well as an insulating body 4 positioned primarily in the housing shaft 3 of the valve housing 1.

The valve that is insertable in a canal 5 of a medical instrument 6, which is only suggestively indicated in FIG. 2, serves to insulate against a distal-side fluid the canal 5 that is configured in the medical instrument 6, in particular an endoscopic instrument, and that serves as input for at least one additional medical instrument. The canal 5 that serves as input for at least one additional medical instrument is extended by the inside of the valve, as can likewise be seen from FIG. 2.

Figure 3:
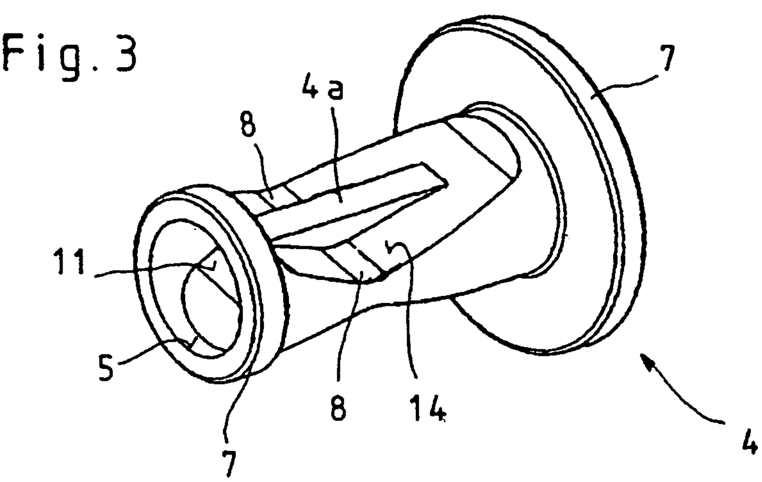
FIG. 3 shows a perspectival view of the insulating body shown in FIG. 2.
Figure 4:
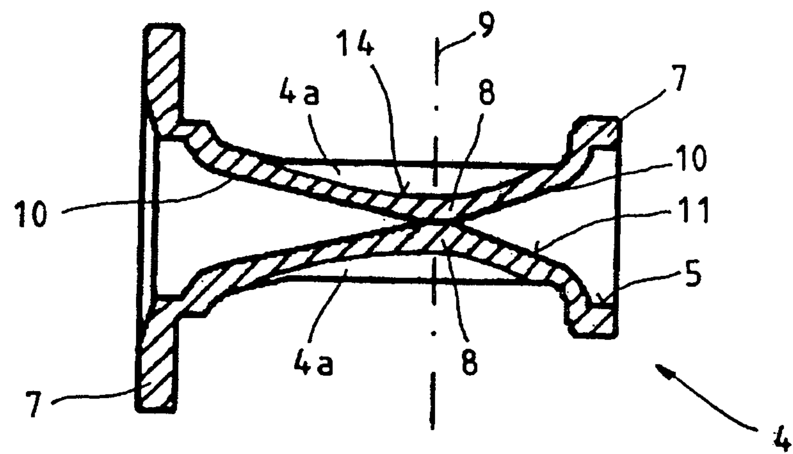
FIG. 4 shows a longitudinal section through the insulating body seen in FIG. 3.

The insulating body 4 positioned in the valve housing 1, manufactured in an elastic material, has, as can be seen in particular from FIGS. 3 and 4, one surrounding flange 7 on both the proximal and its distal sides in order to be able to position the insulating body 4 immovably in the valve housing 1, and the flanges 7 can also be square in configuration, contrary the depiction in FIG. 3

The actual insulating function of the insulating body 4 is assumed by two insulating lips 8 arranged opposite to one another and configured on the inside of the insulating body 4, and which are contiguous to one another in at least linear shape in the closed position of the valve shown in FIG. 4 that insulates the canal 5. To keep rigid the insulating body 4, and especially the insulating lips 8, the insulating body 4 has outwardly positioned stiffening webs 4*a*, as can be seen in particular in the drawing in FIG. 3.

In the illustrated embodiment, the insulating lips 8 are configured as pointing to the middle of the valve housing and essentially convex in cross-section. For the insulating effect of the insulating lips 8 of the insulating body 4, it makes no different whether the insulating lips 8 are configured symmetrically to an axis of symmetry 9 or not. To make possible the insertion of the medical instrument that is to be inserted into the canal 5, the insulating lips 8 include run-up slopes 10 on both sides. Because of the bilateral arrangement of the run-up slopes 10, it is possible to insert the medical instrument that is to be inserted or a guide wire, either from the proximal or from the distal side, into the valve.

Because the mutually contiguous insulating lips 8 of the insulating body 4 are pressed outward and thus in the direction of the open position of the valve, by the fluid pressure on the distal side against the inner surface 11 of the insulating body 4, in the valve housing 1 fluid openings 12 are configured, by which the distal-side fluid can flow into an intermediate space 13 between the outside 14 of the insulating body 4 and the inside of the valve housing 1. This fluid that has flowed into the intermediate space 13 exerts a pressure that is essentially perpendicular to the longitudinal axis of the insulating body 4 and works inward against the insulating body 4, and through this pressure the insulating lips 8 are pressed into their closed position.

The fluid openings 12, which advantageously are configured as slits running as far as the distal-side end of the valve housing 1, can be seen in particular in the perspectival drawing of the valve in FIG. 1. In the illustrated embodiment, three fluid openings 12 are distributed evenly around the circumference of the valve housing 1, ensuring rapid and even build-up of pressure in the intermediate space 13. Of course it is also possible to configure more than three, or fewer than three, fluid openings 12 in the valve housing 1.

To ensure that pressure brought to bear from outside onto the insulating lips 8 constantly provides sufficient insulating effect, the surface of the outside 14 of the insulating body 4 standing in contact with the fluid is arranged so that it at least equal in size to the distal-side inner surface 11 of the insulating body 4 that is impacted with the fluid. Advantageously, however, the surface of the outside 14 of the insulating body 4 standing in contact with the fluid is greater than the distal-side inner surface 11 of the insulating body 4 that is impacted with the fluid.

Figure 5:
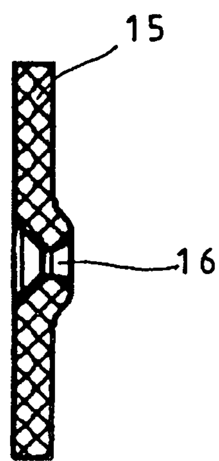
FIG. 5 shows an enlarged view of the insulating element according to FIG. 2 in longitudinal section.

As can further be seen from the sectional view in FIG. 2, in the illustrated embodiment of a valve there is on the proximal side before the aforementioned insulating body 4 an additional insulating element 15, which in this case is configured as a disk insulation equipped with a central opening 16. This additional insulating element 15 seen in FIG. 5 serves to insulate the canal 5 when a medical instrument is inserted into the canal 5. For this purpose the diameter of the opening 16 configured in the disk insulation should be sized so that it is smaller than the outer diameter of the shaft of the medical instrument that is to be inserted into the canal 5.

On the outside of the valve housing 1, an additional insulating element 17 is positioned, which serves to provide anti-fluid insulation with respect to the medical instrument 6 in whose canal 5 the valve can be inserted. To prevent any slippage of the insulating element 17 that is preferably configured as a ring insulation, a circular groove 18 is configured in the valve housing 1 and in this groove the insulating ring can be secured at an exact position. The insulating ring is advantageously configured as an O-ring of silicon. In addition to the insulating function, the insulating element 17 positioned on the outside of the valve housing 1 can also be used as a protrusion that limits the depth of insertion of the valve into the canal 5 of the medical instrument 6 and also it can exert a staying function because of its elasticity.

The valve housing 1 finally includes at least two run-up slopes 19 on the proximal side, which clearly facilitate insertion of the medical instrument that is to be introduced into the canal 5, because a centering of the instrument on the center of the canal is achieved by the run-up slopes 19.

The illustrated valve, along with the uncomplicated structure, is distinguished in that it includes almost the function of a return valve, since the insulating effect of the valve is produced by the same fluid whose exit into the instrument canal 5 is opposed by means of the valve. Contrary to a return valve, the illustrated and described valve can be used on both sides, however.

What is claimed is:

1. A valve for medical instruments for insulating a canal configured in the medical instrument and serving as input for at least one additional medical instrument from a distal-end fluid, the valve comprising:

a valve housing, the valve housing able to be inserted at least partially into the canal;

at least one fluid opening configured in the valve housing; and at least one insulating body positioned in the valve housing, the at least one insulating body including:

a peripheral flange positioned at the proximal end of the insulating body and within the valve housing;

a peripheral flange at the distal end of the insulating body and within the valve housing;

two insulating lips positioned opposite to one another on the inside of the at least one insulating body; and stiffening webs arranged on the outside of the two insulating lips, the stiffening webs serving to press the insulating lips towards one another in a sealing manner by means of the internal tension of the stiffening webs in such a way that the insulating lips are pressed against each other when no additional medical instrument is arranged in the valve housing, wherein the at least one fluid opening is configured so that the distal-side fluid can be conducted out of the canal to the outside of the insulating body in such a way that the distal-side fluid reshapes the insulating body inward, insulating it, to be essentially perpendicular to the longitudinal direction of the insulating body, wherein the insulating lips are pressed against the outer surface of the additional medical instrument when inserted in the valve housing, wherein the distance from the free upper surface of the stiffening webs to the outer surface of the insulating body varies along the longitudinal direction of the stiffening webs in such a way that the distance is largest in an insulating area of the insulating lips, wherein the insulating body is secured free of tension and unspreaded in the longitudinal direction in a fixed position in the valve housing via one of the integrally formed flanges.

2. The valve of claim 1, wherein the at least one fluid opening is configured as a slit running in the axial direction of the valve housing.

3. The valve of claim 2, wherein in the valve housing there are configured several, preferably three, slits evenly distributed around the circumference of the valve housing and extending as far as the distal-side end of the valve housing.

4. The valve of claim 1, wherein the surface of the outside of the insulating body standing in contact with the fluid is greater than the distal-side inside surface of the insulating body that is impacted with the fluid.

5. The valve of claim 1, wherein the two insulating lips configured and are in contact with one another in the closed position at least in linear shape insulating the canal.

6. The valve of claim 5, wherein the insulating lips are configured in one-piece construction with the insulating body.

7. The valve of claim 5, wherein the insulating body and the insulating lips are made of the same material.

8. The valve of claim 5, wherein the insulating lips are configured to be convex in cross-section and essentially pointing toward the middle of the valve housing.

9. The valve of claim 5, wherein run-up slopes are configured on both sides of the insulating lips.

10. The valve of claim 1, wherein the insulating body is secured immovably in the valve housing by means of at least one reshaped flange.

11. The valve of claim 1, wherein at least one additional insulating element is secured in the valve housing on the proximal side before the insulating body.

12. The valve of claim 11, wherein the at least one additional insulating element is configured as a disk insulation equipped with an opening positioned essentially centrally.

13. The valve of claim 12, wherein the diameter of the opening configured in the disk insulation is smaller than the outer diameter of a medical instrument that is to be inserted through this opening.

14. The valve of claim 11, wherein the additional insulating element is configured as a one-piece unit with the insulating body.

15. The valve of claim 1, wherein at least one insulating element is positioned on the outside of the valve housing.

16. The valve of claim 15, wherein the insulating element positioned on the outside of the valve housing is configured as an insulating ring that is secured in a circular groove configured in the valve housing.

17. The valve of claim 16, wherein the insulating ring is an O-ring made of silicon.

18. The valve of claim 1, wherein run-up slopes are formed on at least the proximal side of the valve housing.

19. The valve of claim 1, wherein the stiffening webs are configured in one piece construction within the insulating body.

20. The valve of claim 1, wherein the stiffening webs extend substantially along the outside of the insulating lips from approximately a proximal end of the insulating lips to approximately a distal end of the insulating lips.

21. The valve of claim 1, wherein the stiffening webs have a smaller width than the insulating lips along the longitudinal direction of the insulating body.

22. The valve of claim 1, wherein there are only two stiffening webs arranged on the outside of the two insulating lips, each of the two stiffening corresponding to a respective insulating lip.

23. A valve for medical instruments for insulating a canal configured in the medical instrument and serving as input for at least one additional medical instrument from a distal-end fluid, the valve comprising:

a valve housing, the valve housing able to be inserted at least partially into the canal;

at least one fluid opening positioned in the valve housing, the at least one insulating body including:

a peripheral flange at the proximal end of the insulating body and within the valve housing;

a peripheral flange at the distal end of the insulating body and within the valve housing;

two insulating lips positioned opposite to one another on the inside of the at least one insulating body; and stiffening webs arranged on the outside of the two insulating lips, the stiffening webs serving to press the insulating lips towards one another in a sealing manner by means of the internal tension of the stiffening webs in such a way that the insulating lips are pressed against each other when no additional medical instrument is arranged in the valve housing, wherein the at least one fluid opening is configured so that the distal-side fluid can be conducted out of the canal to the outside of the insulating body in such a way that the distal-side fluid reshapes the insulating body inward, insulating it, to be essentially perpendicular to the longitudinal direction of the insulating body, wherein the insulating lips are pressed against the outer surface of the additional medical instrument when inserted in the valve housing, wherein the distance from the free upper surface of the stiffening webs to the outer surface of the insulating body varies along the longitudinal direction of the stiffening webs in such a way that the distance is largest in an insulating area of the insulating lips, wherein the insulating body is secured free of tension and unspreaded in the longitudinal direction in a fixed position in the valve housing via one of the integrally formed flanges, wherein at least one additional insulating element can be secured in the valve housing on the proximal side before the insulating body, and wherein the additional insulating element is securely connected with the insulating body, in particular by cementing.

24. A valve for medical instruments for insulating a canal configured in the medical instrument and serving as input for at least one additional medical instrument from a distal-end fluid, the valve comprising:

a valve housing, the valve housing able to be inserted at least partially into the canal;

at least one fluid opening configured in the valve housing; and at least one insulating body positioned in the valve housing, the at least one insulating body including:

a peripheral flange positioned at the proximal end of the insulating body and within the valve housing;

a peripheral flange at the distal end of the insulating body and within the valve housing;

two insulating lips positioned opposite to one another on the inside of the at least one insulating body, the insulating lips configured in one-piece construction with the insulating body; and stiffening webs arranged on the outside of the two insulating lips, the stiffening webs serving to press the insulating lips towards one another in a sealing manner by means of the internal tension of the stiffening webs in such a way that the insulating lips are pressed against each other when no additional medical instrument is arranged in the valve housing, wherein the at least one fluid opening is configured so that the distal-side fluid can be conducted out of the canal to the outside of the insulating body in such a way that the distal-side fluid reshapes the insulating body inward, insulating it, to be essentially perpendicular to the longitudinal direction of the insulating body, wherein the insulating lips are pressed against the outer surface of the additional medical instrument when inserted in the valve housing, wherein the distance from the free upper surface of the stiffening webs to the outer surface of the insulating body varies along the longitudinal direction of the stiffening webs in such a way that the distance is largest in an insulating area of the insulating lips, wherein the insulating body is secured free of tension and unspreaded in the longitudinal direction in a fixed position in the valve housing via one of the integrally formed flanges, wherein the surface of the outside of the insulating body standing in contact with the fluid is greater than the distal-side inside surface of the insulating body that is impacted with the fluid.

25. The valve of claim 24, wherein the insulating lips are configured to be convex in cross-section and essentially pointing toward the middle of the valve housing.

26. The valve of claim 25, wherein run-up slopes are configured on both sides of the insulating lips.

27. The valve of claim 24, wherein the peripheral flanges are square in configuration.

28. The valve of claim 24, wherein the fluid flows into an intermediate space between the outside of the insulating body and the inside of the valve housing.

29. The valve of claim 28, wherein the fluid exerts a pressure that is essentially perpendicular to the longitudinal axis of the insulating body and works inward against the insulating body, and through the pressure, the insulating lips are pressed into a closed position.

30. The valve of claim 29, wherein the surface of the outside of the insulating body standing in contact with the fluid is arranged so that it is at least equal in size to the distal-side inner surface of the insulating body that is impacted with the fluid.

31. The valve of claim 29, wherein the surface of the outside of the insulating body standing in contact with the fluid is arranged so that it is greater in size to the distal-side inner surface of the insulating body that is impacted with the fluid.

* * * * *